| United States Patent [19] | [11] Patent Number: 4,724,138 |
| --- | --- |
| Duffy et al. | [45] Date of Patent: Feb. 9, 1988 |

[54] PREPARATION OF A SELF SUPPORTING COSMETIC FROM A PIGMENTED POWDER

[75] Inventors: John A. Duffy, West Milford, N.J.; Richard D. Katstra, Warwick, N.Y.

[73] Assignee: Avon Products, Inc., New York, N.Y.

[21] Appl. No.: 935,058

[22] Filed: Nov. 20, 1986

Related U.S. Application Data

[63] Continuation of Ser. No. 430,350, Sep. 30, 1982, abandoned.

[51] Int. Cl.$^4$ .................... A61K 7/021; A61K 7/42; A61K 7/32; A61K 7/035
[52] U.S. Cl. .................................. 424/63; 424/59; 424/60; 424/65; 424/69; 424/DIG. 5; 514/844
[58] Field of Search .............. 424/59, 60, 63, 65, 424/69, DIG. 5; 514/844; 106/111, 114

[56] References Cited

U.S. PATENT DOCUMENTS

| 2,322,930 | 3/1940 | Gardner et al. | 106/114 |
| 3,800,034 | 12/1970 | Kircher et al. | 424/DIG. 5 X |
| 3,912,528 | 10/1975 | Doan et al. | 106/114 |
| 3,966,479 | 6/1976 | Koblitz | 106/111 |
| 4,128,630 | 12/1978 | Hayashi et al. | 424/69 |
| 4,287,103 | 9/1981 | Green et al. | 106/114 |
| 4,298,394 | 11/1981 | Leeming et al. | 106/114 |
| 4,299,790 | 11/1981 | Greenberg | 106/114 |
| 4,332,763 | 6/1982 | Hempel et al. | 424/DIG. 5 X |

FOREIGN PATENT DOCUMENTS

| 36698 | 3/1981 | European Pat. Off. | 424/63 |
| 45-36595 | 11/1970 | Japan | 424/63 |
| 57-38707 | 3/1982 | Japan | 424/63 |

Primary Examiner—David M. Naff
Assistant Examiner—Shawn P. Foley
Attorney, Agent, or Firm—S. Michael Bender

[57] ABSTRACT

Coherent powder compositions are formed by blending a powder phase containing at least 5 weight percent calcium sulfate hemihydrate with a liquid phase containing sufficient water to fully convert the hemihydrate to calcium sulfate dihydrate and drying the resultant blend. Uniformly pigmented products are formed by including a powdered pigment in the powder phase and 0.1 to 4.0 weight percent surfactant in the aqueous phase. Compositions suitable for use as cosmetic sticks are formed by employing at least 40 weight percent calcium sulfate hemihydrate. Preferably the products are formed by combining 40 to 60 parts by weight of aqueous phase with 50 parts by weight of powder phase. To improve pay-off characteristics the products are subjected to a temperature above 128° C., the outer surface is abraded or up to 20 weight percent of the aqueous phase is glycerin or propylene glycol.

2 Claims, No Drawings

PREPARATION OF A SELF SUPPORTING COSMETIC FROM A PIGMENTED POWDER

This application is a continuation of application Ser. No. 430,350, filed 9/30/82, now abandoned.

BACKGROUND OF THE INVENTION (a) Field of the Invention

This invention relates to solid shaped powder compositions which are formed without resort to high pressure and which can be pigmented. The compositions may be employed in cosmetic applications, such as eye shadows or rouge.

(b) State of the Art

Solid powder products, particularly powder pigments used to form rouge or eye shadows, desirably contain little or no oils or waxes since dry powdered products exhibit less creasing than oil or wax containing products. Wax and oil based products are difficult to apply evenly and with the desired precision. Further, after application, these products may smear or be transferred from one surface to another, as from the eyelid to the brow area.

Conventional solid powder products have been formed by combining low levels of oils, waxes and other binders with the powder particles and subjecting the particles to high pressures. Processing of these conventional products poses difficulties since the small amounts of binder, e.g., 5–10 weight percent oil or wax, must be deposited evenly on the powder particles to insure formation of a coherent mass. The extensive beating occurring during mixing to insure uniform deposition of the binder on the powder is detrimental to some pigments. For example, pearl pigments which are of relatively large particle size are broken down. Also, pigment shade may be altered by beating during the mixing process.

Oil or wax-free powder sticks have not proven successful since those with adequate strength exhibit poor pay-off properties during use by the consumer, i.e., pay-off requires too high an application pressure. Further, the compaction step has severely circumscribed the forms into which a solid powder product can be shaped.

In some cases, it is desirable to pigment solid powder compositions, for example, when forming eyeshadows and the like. In these cases, the pigment should be uniformly distributed throughout the powder and mottling is desirably avoided. However, pigments contain residual oils which may result in a mottled appearance.

It has now been discovered that wax and oil-free solid powder products can be formed without resorting to high pressure compaction. The products can be molded to any desired shape. Further, the products have adequate strength and good pay-off when in stick or other free standing form and can be pigmented uniformly.

SUMMARY OF THE INVENTION

This invention relates to coherent powder compositions having utility as pigmented cosmetics, talc sticks, fragranced pomanders and the like. The compositions are formed by blending a powder phase containing at least 5 weight percent calcium sulfate hemihydrate with an aqueous phase containing sufficient water to fully hydrate the hemihydrate and then drying the blended phases. Uniformly pigmented products are formed by including in the powder phase a powder pigment, preferably in an amount equal to 40 to 60 weight percent of the powder phase and including 0.1 to 4.0 weight percent surfactant, preferably a mixture of sorbitan monostearate and polyoxyethylene (20) sorbitan monostearate in the aqueous phase. By incorporation of at least 40 weight percent calcium sulfate hemihydrate into the powder phase, products which are self-supporting can be formed. In those cases where the compositions of the invention are cosmetic products, the hemihydrate is no more than 70 weight percent of the powder phase. Improved pay-off is achieved if the products are subjected to temperatures above 128° C., are abraded or the aqueous phase includes up to 20 weight percent glycerin or propylene glycol. The products may be shaped simply by pouring the blended phases into molds and allowing the mixture to set. The set products may be dried in the molds or may be removed therefrom to completely dry.

DETAILED DESCRIPTION OF THE INVENTION

The present invention provides compositions and methods for forming coherent powder products. In practice of the invention, calcium sulfate hemihydrate is hydrated to calcium sulfate dihydrate. As a result of the hydration, a powder composition containing the hemihydrate sets to a coherent powder.

More specifically, in the practice of the present invention, a powder phase containing at least five weight percent calcium sulfate hemihydrate is homogeneously blended with an aqueous phase containing sufficient water to fully hydrate the hemihydrate. The blended phases set to a hard mass which in turn is fully dried.

The coherent powder compositions which are formed in the practice of the invention have application as powdered cosmetic products, such as rouge or eyeshadow, as talc sticks, and as pomanders. Depending upon the use to which the invention is put, the materials used to form the coherent products and the proportions thereof are adjusted. In particular, where pigmented products are formed a powdered pigment is included in the powder phase and to produce uniform color a surfactant is included in the aqueous phase. When self-supporting products such as cosmetic sticks or pomanders are formed, the powder phase contains at least 40 weight percent calcium sulfate hemihydrate in order to achieve sufficient strength. When pay-off from the final product is required, as in cosmetic applications, the powder phase contains no more than 70 weight percent calcium sulfate hemihydrate to avoid too hard a product. In addition, drying treatments, surface abrasion or additives can be employed to improve pay-off.

The calcium sulfate hemihydrate generally may be any hemihydrate commercially available. For example, the following plasters have been found acceptable: #1 Molding Plaster (Oklahoma), #1 Molding Snap Set (Oklahoma), #1 Molding Snap Set (Maryland) and Hydrocal Snap Set (Oklahoma) all from U.S. Gypsum and Plaster of Paris from Durabond.

All of these materials appear to work equally well in formulations of the invention. However, plasters from Oklahoma are preferred because of their higher degree of purity and color (whiteness). #1 Molding plaster from Oklahoma is most preferred because of its low cost, high purity and uniform color (whiteness).

Hydrocal plasters will tolerate larger amounts of water than molding plasters without loss of cohesive strength for low water/plaster ratios. However, since systems of the invention incorporate high water/plaster ratios, this advantage is lost. Snap set plasters are those that have been modified to exhibit specific altered viscosity profiles during the hydration reaction. This is most noticeable with low water/plaster ratios. Again, this effect is minimized due to high water/plaster ratios in the invention systems.

The powder employed in formation of the products of the invention may contain a variety of other materials in addition to the hemihydrate. For example, talc, mica, corn starch, kaolin, metal soaps, antiperspirants, UV absorbers, preservatives, pigments, pigment extenders or other conventional cosmetic powders, alone or in combination, may comprise the balance of the powder phase. Materials which accelerate or retard setting may also be included in the powder phase. In the case of pigmented cosmetic products, the pigment preferably is 40 to 60 weight percent of the powder phase.

The liquid phase of the invention contains sufficient water to hydrate the hemihydrate to the dihydrate. This requires a minimum of 18.6 weight percent water based on the amount of hemihydrate employed. The liquid phase additionally may contain surfactants, emollients, humectants, fragrances or other desired hydrophobic or hydrophilic ingredients.

The products of this invention are prepared by first blending the calcium sulfate hemihydrate with the remaining components of the powder phase using conventional powder blending techniques. The liquid phase is prepared by adding the surfactant or any other ingredients to the water and blending. Depending on the ingredients chosen, heating may be necessary to achieve a homogeneous mixture of the aqueous phase. The powder phase is then blended with the aqueous phase until a homogeneous mixture is achieved.

The mixture may be extruded, stamped or cast into any desired shape or form. For example, cosmetic products may be poured to form conventional pan-type products or may be extruded or molded as sticks. The ratio of powder phase to aqueous phase is adjusted according to the selected processing technique. High powder to water ratios will result in a damp powder more suitable for extrusion or stamping. Low powder to water ratios produce free-flowing slurries suitable for casting into molds. Generally 40 to 60 parts by weight of the aqueous phase are blended with 50 parts by weight of the powder phase. Above 60 parts aqueous phase the products lack cohesive strength for forming, while below 40 parts the slurry is not free flowing. In most preferred procedures, equal parts by weight are blended.

Upon mixing the powder and aqueous phases, the calcium sulfate hemihydrate hydrates to its dihydrate structure according to the following reaction:

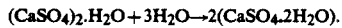

$$(CaSO_4)_2.H_2O + 3H_2O \rightarrow 2(CaSO_4.2H_2O).$$

During the reaction, the cast, extruded or stamped piece sets to a hard mass. The pieces are then dried to remove any excess water. In the case of molded products drying may be effected in the mold or the product may be removed from the mold after setting to a handleable mass and then dried.

As noted, in producing pigmented products a surfactant is necessary to effect a uniform color distribution. Without the surfactant, a mottled appearance is produced due to residual oily materials in the pigments which upon mixing with the aqueous phase migrate toward the surface of the product. The surfactant emulsifies or otherwise affects the oil-like materials and prevents mottling. Typically surfactant levels of 0.1 to 4.0 weight percent of the aqueous phase produce uniform color distribution.

Surfactants may also be incorporated into the products of the invention to serve as dispersants and processing aids which reduce the viscosity of the slurry formed when the aqueous and powder phases are blended. Surfactants may also serve to emulsify emollients, fragrances or other ingredients into the aqueous phase.

The surfactant is selected according to its function and the ingredients present. Generally, its HLB must be compatible with the materials being dispersed. Nonionic surfactants have generally been found suitable for purposes of producing uniformly colored products in the practice of this invention. Surfactants that are highly water soluble (typically the anionics and cationics) may also be employed; however, they are not preferred since they tend to migrate toward the drying surface during removal of the excess water and in some cases, the surfactant will be observed on the dried surface of the product.

Examples of suitable surfactants are as follows (parenthetical expressions refer to trademarks under which the surfactants are sold and the source companies):

polyoxyethylene 4 lauryl ether (Brij 30-ICI), polyoxyethylene 10 cetyl ether (Brij 56-ICI), glycerol monostearate and polyoxyethylene stearate (Arlacel 165-ICI), sorbitan monostearate (Span 60-ICI), polyoxyethylene 20 sorbitan monolaurate (Tween 20-ICI), polyoxyethylene 20 sorbitan monostearate (Tween 60-ICI), polyglycols (Pluronic 31R1-BASF), nonylphenoxypoly(ethyleneoxy)ethanol (Igepal CO-720-GAF), sodium lauryl sulfate, and poly[N-[3-(dimethylammonio)-propyl]-N'-[3-(ethyleneoxyethylene dimethylammonio propyl]urea dichloride] (Mirapol A-15-Miranol)

Preferred surfactants are combinations of low and high HLB surfactants, specifically Span 60 with Tween 60. Varying the ratio of Span 60 to Tween 60 provides the flexibility of adjusting the total HLB to optimize both the emulsification of residual oils and the slurry viscosity. This optimum HLB varies depending on what ingredients are employed.

In summary, a pigmented product may be formed by blending a powder phase containing a powder material including a powdered pigment and at least five weight percent calcium sulfate hemihydrate and an aqueous liquid phase comprising water sufficient to fully hydrate the calcium sulfate and 0.1 to 4.0 weight percent surfactant and allowing the blended phases to dry. In preferred practice for cosmetic products, the pigment is at least 40 to 60 weight percent of the powder phase. The preferred surfactant is a nonionic surfactant, most preferably a mixture of sorbitan monostearate and polyoxyethylene (20) sorbitan monostearate which optimally are in a weight ratio of six to four.

In forming self-supporting coherent powder products, a powder phase containing at least 40 weight percent calcium sulfate hemihydrate is homogeneously blended with an aqueous phase containing water sufficient to convert the hemihydrate to the dihydrate and drying the blended phases. This results in a solid powder product containing at least 44 weight percent of the dihydrate. This product optionally may contain pigments, surfactants or the like.

When cosmetic products are formed in the practice of the invention, pay-off can be an important factor. In general, no more than seventy weight percent of the powder phase should be the hemihydrate to avoid formation of products requiring extremely high pressure for pay-off. Thus, dried products containing less than 73 weight percent dihydrate may be employed as cosmetics requiring pay-off properties.

Drying of the products of the invention may be effected at ambient conditions or in a microwave oven. In these cases, however, outer surfaces of the dried products which are exposed to the air are extremely hard and pay-off may require excessive pressures. It has been discovered that drying the products of the invention at temperatures in excess of 128° C. results in products with good pay-off characteristics. Alternatively, the dried products may be subjected to temperatures above 128° C. until the hard outer surface is removed; i.e., has softened so that good pay-off at reasonable pressure is possible. Typically, exposure to temperatures above 128° C. for periods of 20 minutes are sufficient to remove the hard surface and produce a product with improved pay-off properties. The heating may improve pay-off by reversing the hydration reaction. Extended periods of heating result in higher payoff with a decrease in strength although cohesiveness is retained.

The outer shell may also be removed by abrading the outer surface of the product, as by sharpening an eyeshadow stick. Finally, incorporation of up to 20 weight percent glycerin or propylene glycol into the aqueous phase results in a product which exhibits good pay-off characteristics without additional heating steps.

The following examples are illustrative of the invention. References to quantities are parts by weight unless otherwise indicated.

EXAMPLE 1

A pigmented molded product was made using the following powder and aqueous phases:

| Powder Phase | Parts | Aqueous Phase | Parts |
| --- | --- | --- | --- |
| Talc | 19.75 | Water | 39.60 |
| Ultramarine Blue Pigment | 10.00 | Arlacel 165 (ICI) | 0.40 |
| Methyl Paraben | 0.25 | | |
| Calcium Sulfate Hemihydrate | 20.00 | | |

The ingredients comprising the powder phase were added to a suitable container and osterized until a homogeneous mixture was achieved. The aqueous phase was prepared by adding the Arlacel 165 to water heated to 60° C. The powder phase was mixed with the aqueous phase at 60° C. and stirred until a smooth, homogeneous mixture was obtained. The resulting mixture, a free-flowing slurry, was poured into molds and allowed to set to a hard mass. The pieces were then removed from the molds and dried in a conventional oven at 130° C. The pieces exhibited good cohesive strength and excellent pay-off when rubbed on the skin.

EXAMPLE 2

Eyeshadow sticks were prepared by mixing the following powder and aqueous phases and pouring the resulting slurry into cylindrical molds. After setting to a hard mass, the sticks were removed from the molds and dried in a conventional oven for approximately 3 hours at 130°–135° C.

| | | Parts |
| --- | --- | --- |
| Powder Phase: | #1 Molding Plaster | 20.00 |
| | Methyl Paraben | .25 |
| | Pigment Blend | 29.75 |
| Aqueous Phase: | Water | 48.57 |
| | Span 60 (ICI) | .57 |
| | Tween 60 (ICI) | .86 |

| | Pigment Blends: | Parts | Parts | Parts |
| --- | --- | --- | --- | --- |
| Blue: | Ultramarine Blue | 10.00 | 10.00 | |
| | Titanium Dioxide Coated Mica | 19.75 | 14.75 | |
| | Bismuth Oxychloride | — | 5.00 | |
| Wine: | Mica | 4.40 | 4.40 | |
| | Iron Oxide Red | .97 | .97 | |
| | Cosmetic Brown | .39 | .39 | |
| | Ultramarine Blue | 3.07 | 3.07 | |
| | Titanium Dioxide Coated Mica | 9.60 | 4.85 | |
| | Cloisonne Rouge Flambe | 6.47 | 6.47 | |
| | Cloisonne Red | 4.85 | 4.85 | |
| | Bismuth Oxychloride | — | 4.75 | |
| Slate: | Titanium Dioxide Coated Mica | 25.00 | 20.00 | |
| | Iron Oxide Black | 4.75 | 4.75 | |
| | Bismuth Oxychloride | — | 5.00 | |
| Green: | Titanium Dioxide Coated Mica | 9.75 | 14.75 | 9.75 |
| | Ultramarine Blue | 1.73 | 1.73 | 1.73 |
| | Dark Blue | 9.34 | 9.34 | 9.34 |
| | Iron Oxide Yellow | 1.27 | 1.27 | 1.27 |
| | Cosmetic Green | 7.66 | 2.66 | 2.66 |
| | Bismuth Oxychloride | — | — | 5.00 |

The sticks exhibited good cohesive strength and excellent pay-off.

EXAMPLE 3

Employing the procedure of Example 2 a cheek blush stick was prepared from the following powder and aqueous phases:

| | Parts | | |
| --- | --- | --- | --- |
| | 1 | 2 | 3 |
| Powder Phase: | | | |
| #1 Molding Plaster | 24.75 | 22.50 | 20.00 |
| Methyl Paraben | .25 | .25 | .25 |
| Iron Oxide Yellow | 1.40 | 1.40 | 1.40 |
| D & C Red #7 | 1.30 | 1.30 | 1.30 |
| Iron Oxide Red | .65 | .65 | .65 |
| Timica Silk White | 21.65 | 21.65 | 21.65 |
| Talc | — | 2.25 | 4.75 |
| Aqueous Phase: | | | |
| Water | 48.57 | 48.57 | 48.75 |
| Tween 60 (ICI) | .86 | .86 | .86 |
| Span 60 (ICI) | .57 | .57 | .57 |

EXAMPLE 4

A body talc stick was prepared according to the procedure of Example 2 employing the following ingredients.

| | Parts | | | |
| --- | --- | --- | --- | --- |
| | 1 | 2 | 3 | 4 |
| #1 Molding Plaster | 20.00 | 20.00 | 25.00 | 25.00 |
| Methyl Paraben | .25 | .25 | .25 | .25 |
| Talc | 19.75 | 14.75 | 14.75 | 9.75 |
| Microencapsulated Mineral Oil | 10.00 | 15.00 | 10.00 | 15.00 |

-continued

| | Parts | | | |
|---|---|---|---|---|
| | 1 | 2 | 3 | 4 |
| Aqueous Phase | 45.00 | 42.00 | 40.00 | 40.00 |

In each instance the aqueous phase contained 34.00 parts water, 0.40 parts Span 60 (ICI) and 0.60 parts by weight Tween 60 (ICI).

EXAMPLE 5

A fragranced pomander was prepared from the following powder and aqueous phases:

| Powder Phase: | #1 Molding Plaster Snap Set-Oklahoma | 90.00 |
|---|---|---|
| | | Parts |
| Aqueous Phase: | Water | 42.00 |
| | Tween 60 (ICI) | 1.10 |
| | Strawberry Fragrance | 10.00 |
| | Span 60 (ICI) | .50 |

The aqueous phase was prepared by adding the Tween 60 to the water and the Span 60 to the fragrance. The two combinations were heated approximately 45° C. and then mixed, thereby emulsifying the fragrance into water.

The powder phase was then mixed with the carrier phase and the resulting slurry was poured into molds. After setting to a hard mass, the pieces were removed from the molds and dried in a microwave oven for 30 minutes. The dried pieces exhibited excellent fragrance rendition.

EXAMPLE 6

Potassium sulfate and sodium sulfate have been tested as accelerators. Accelerators are additives that reduce the time required for the slurry formed by combining the aqueous and powder phases to form a hard mass. Potassium sulfate is the more efficient of the two and is the preferred accelerator. Sodium citrate has been tested as a retarder.

Various amounts of retarder or accelerator were added to a powder phase and mixed with water. The powder phase was as follows:

| Ingredient | Parts |
|---|---|
| #1 Molding plaster | 15.00 |
| Sodium lauryl sulfate | .25 |
| Mica | 29.75 |
| Corn Starch Ester | 5.00 |

The time required for a hard mass to form was recorded. The results are set forth below.

| Powder Phase | Water | Potassium Sulfate | Sodium Citrate | Set Time |
|---|---|---|---|---|
| 50 | 50 | — | — | 25 minutes |
| 50 | 50 | 1.0 | — | 5 minutes |
| 50 | 50 | 3.5 | — | 3 minutes |
| 50 | 50 | — | .5 | 2 hours |

EXAMPLE 7

Coherent powder products were prepared employing the following ingredients:

| | Ingredients | Parts |
|---|---|---|
| Powder Phase: | #1 Molding Plaster | 25.00 |
| | Methyl Paraben | .25 |
| | Coated Mica - Pale Gold | 9.19 |
| | Coloron - Red Brown | 2.47 |
| | Iron Oxide Red | 1.23 |
| | Cosmetic Brown | .62 |
| | Iron Oxide Yellow | 1.03 |
| Aqueous Phase: | Water | 79.00 |
| | Propylene Glycol | 20.00 |
| | Span 60 | .40 |
| | Tween 60 | .60 |

50 parts of the powder phase were mixed with 50 parts of the aqueous phase and poured into plastic compacts. After approximately one hour, one compact was dried in a microwave oven until its weight was constant (free water removed). The second sample was allowed to dry at ambient conditions for approximately 72 hours. Both samples exhibited good pay-off, in contrast to samples containing no propylene glycol, which required heat treatment above 128° C. to achieve good pay-off.

We claim:
1. A method of forming a pigmented cosmetic powder product comprising:
   (a) blending 50 parts by weight of a powder phase comprising a cosmetic powder material containing up to 60 weight percent of pigment and between 40 to 70 weight percent calcium sulfate hemihydrate with 40 to 60 parts by weight of an aqueous phase comprising 0.1 to 4.0 weight percent surfactant and sufficient water to fully hydrate the calcium sulfate hemihydrate; and
   (b) drying the blended phases by exposure to an ambient temperature of not less than about 128° C. for a period of time of not less than about 20 minutes to form a self supporting powder product having an outer surface soft enought to exhibit good to excellent pay-off characteristics.
2. The product produced by the method of claim 1.

* * * * *